(12) United States Patent
Star-Lack et al.

(10) Patent No.: US 7,940,891 B2
(45) Date of Patent: May 10, 2011

(54) METHODS AND SYSTEMS FOR TREATING BREAST CANCER USING EXTERNAL BEAM RADIATION

(75) Inventors: Josh Star-Lack, Palo Alto, CA (US); David Humber, Los Gatos, CA (US); Karla Knott, Redwood Shores, CA (US); Corey Zankowski, San Jose, CA (US); Michael C. Green, Palo Alto, CA (US); Gary Virshup, Cupertino, CA (US); James Clayton, San Jose, CA (US); Michelle M. Svatos, Oakland, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 155 days.

(21) Appl. No.: 12/256,461

(22) Filed: Oct. 22, 2008

(65) Prior Publication Data

US 2010/0098214 A1    Apr. 22, 2010

(51) Int. Cl.
*A61N 5/00*    (2006.01)
(52) U.S. Cl. .......................................... 378/65; 378/195
(58) Field of Classification Search .............. 378/64–65, 378/193, 195, 196, 197, 198, 208, 209
See application file for complete search history.

(56) References Cited

U.S. PATENT DOCUMENTS

| | | | |
|---|---|---|---|
| 4,705,955 A | 11/1987 | Mileikowsky | |
| 5,078,140 A * | 1/1992 | Kwoh | 600/417 |
| 5,207,223 A | 5/1993 | Adler et al. | |
| 5,418,372 A * | 5/1995 | Schonberg et al. | 250/492.3 |
| 5,999,587 A | 12/1999 | Ning et al. | |
| 6,075,836 A | 6/2000 | Ning | |
| 6,298,110 B1 | 10/2001 | Ning | |
| 6,477,221 B1 | 11/2002 | Ning | |
| 6,480,565 B1 | 11/2002 | Ning | |
| 6,504,892 B1 | 1/2003 | Ning | |
| 6,987,831 B2 * | 1/2006 | Ning | 378/37 |
| 7,085,347 B2 | 8/2006 | Mihara et al. | |
| 7,526,066 B2 | 4/2009 | Koshnitsky et al. | 378/68 |
| 2001/0005410 A1 * | 6/2001 | Rasche et al. | 378/197 |
| 2004/0174949 A1 * | 9/2004 | Yamashita et al. | 378/65 |
| 2006/0193435 A1 | 8/2006 | Hara | |
| 2006/0241727 A1 | 10/2006 | Dowlatshahi | |
| 2006/0262898 A1 * | 11/2006 | Partain et al. | 378/37 |
| 2007/0064867 A1 | 3/2007 | Hansen et al. | 378/37 |

(Continued)

FOREIGN PATENT DOCUMENTS

WO   WO2006119426 A2   11/2006

(Continued)

OTHER PUBLICATIONS

Jozsef et al., "Application of radiosurgery principles to a target in the breast: A dosimetric study," Med. Phys. May 2000, 27(5), pp. 1005-1010.

(Continued)

*Primary Examiner* — Hoon Song
(74) *Attorney, Agent, or Firm* — Houst Consulting

(57) ABSTRACT

A radiation apparatus includes a radiation source movable in translational and/or rotational degrees of freedom, and a structure adapted to support a body. The structure is provided with an opening to allow a portion of the body passing through to be exposed to at least a portion of the therapeutic radiation while in use.

46 Claims, 8 Drawing Sheets

U.S. PATENT DOCUMENTS

2007/0071168 A1* 3/2007 Allison et al. .................. 378/65
2007/0242801 A1* 10/2007 Mackie et al. .................. 378/65
2008/0230074 A1 9/2008 Zneng et al.

FOREIGN PATENT DOCUMENTS

WO WO2008106468 A1 9/2008

OTHER PUBLICATIONS

PCT, International Search Report and Written Opinion of the International Searching Authority in PCT/US2009/058662, Apr. 30, 2010, 13 pages.

* cited by examiner

METHODS AND SYSTEMS FOR TREATING BREAST CANCER USING EXTERNAL BEAM RADIATION

TECHNICAL FIELD

This invention relates in general to radiation treatment of diseases and in particular to radiation systems and methods useful in diagnosis and treatment of breast cancer.

BACKGROUND

It is estimated that as many as 80% of women diagnosed with breast cancer may be eligible for breast cancer conservation (BCT) therapy. Numerous clinical trials have demonstrated that survival rates are increased if surgical removal of the tumor (lumpectomy) is followed by radiation therapy. Whole-breast external beam fractionated radiation therapy, often coupled with a boost dose to the tumor region, is now the clinically accepted standard-of-care.

Despite the high indication rate for cancer conservation therapy, many women still opt for mastectomy. This is partly due to the inconvenience of the fractionated treatment regimen which may last up to six weeks. The associated time commitment and logistical difficulties associated with daily travel may discourage a number of women from choosing cancer conservation therapy.

Accordingly, to significantly reduce the cost of treatment in general and encourage more patients to adopt cancer conservation therapy, there is a need for radiation treatment systems that require less capital equipment and infrastructure costs associated with building new treatment center closer to patients' residence. There is also a need for radiation therapy that requires reduced number of treatment fractions. Research into accelerated partial breast irradiation using interventional techniques such as MammoSite® has shown some promise. This has spurred encouraging investigations into hypo-fractionation using external beams such as intensity-modulated radiation therapy (IMRT).

SUMMARY

A radiation apparatus is provided comprising a radiation source movable in a translational direction, and a structure adapted to support a body. The structure is provided with an opening to allow a portion of the body passing through to be exposed to at least a portion of the radiation while in use. The radiation apparatus may be constructed with small form factors, self-shielded or self-contained, and provides more efficient and advanced radiation therapy and imaging.

In some embodiments, the radiation source is movable in three translational directions. In some embodiments, the radiation source is movable in both translational and rotational degrees of freedom. In a preferred embodiment, the radiation source is movable in three translational and three rotational degrees of freedom. In some embodiments, the radiation source is adapted to generate a therapeutic radiation suitable for treatment of cancer. In some embodiments, the radiation source is capable of generating a therapeutic radiation and a diagnostic radiation.

The structure can be in various forms or shapes and adapted to support the body such as a patient in a variety of positions or orientations such as prone, lying on side, forward-leaning, standing, or seated positions. The opening is adapted to allow a portion of the body such as a patient's breast or a patient's breast and its auxiliary tissue passing through.

In some embodiments, the radiation apparatus further includes a second radiation source adapted to generate a radiation suitable for imaging e.g. at a kilo-volt energy level and an image detector disposed opposite to the second radiation source. The second radiation source and image detector may be disposed on a same side of the structure. Alternatively, the second radiation source and the image detector may be disposed on opposite sides of the structure.

In some embodiments, a radiation apparatus comprises a radiation source capable of generating a radiation for therapeutic treatment, and a structure adapted to support a body. The structure is provided with an opening to allow a portion of the body passing through to be exposed to at least a portion of the radiation while in use. The radiation source is adapted to be rotatable about a substantially vertical axis.

In one aspect, an apparatus for radiation treatment of breast cancer includes a structure adapted to support a patient in a position and provided with an opening to allow a breast of the patient passing through. The apparatus includes a radiation source configured to generate a therapeutic radiation to the breast. The radiation source is movable in translational and rotational degrees of freedom, thereby being capable of delivering at least a portion of the therapeutic radiation to at least a portion of the breast at an adjustable distance between the radiation source and the breast, from an adjustable angle to the breast, and/or in an adjustable trajectory.

In one aspect, a radiation method comprises positioning a body on a structure which is provided with an opening allowing a portion of the body passing through, and delivering a therapeutic radiation to the body portion using a radiation source that is movable at least in a translational direction.

In some embodiments, the radiation is delivered using a radiation source that is movable in three translational directions. In some embodiments, the radiation is delivered using a radiation source that is movable in both translational and rotational degrees of freedom. In a preferred embodiment, the radiation is delivered using a radiation source that is movable in three translational and three rotational degrees of freedom.

In some embodiments, the intensity of the radiation is modulated. In some embodiments, the radiation is delivered in an arc geometry.

In some embodiments, the method further comprises delivering a radiation for imaging the breast, and acquiring a data set using the imaging radiation. The radiation for imaging can be delivered in a linear geometry or in an arc geometry.

BRIEF DESCRIPTION OF THE DRAWINGS

These and various other features and advantages of the present invention will become better understood upon reading of the following detailed description in conjunction with the accompanying drawings and the appended claims provided below, where:

DETAILED DESCRIPTION OF VARIOUS EMBODIMENTS

Figure 1:
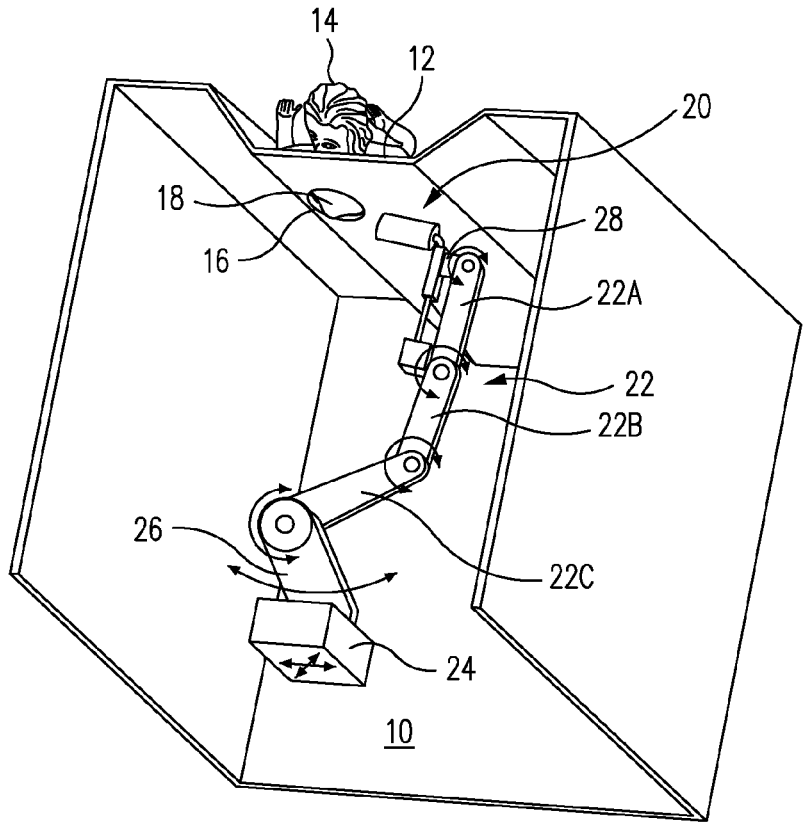
FIG. 1 illustrates a radiation system in accordance with some embodiments of the invention.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. For instance, various embodiments of the invention are described in connection with radiation treatment of breasts of human patients. It will be appreciated that the claimed invention may be used on animals as well as humans, and may be used on different body parts.

Radiation System Overview

FIG. 1 illustrates a radiation apparatus 10 in accordance with some embodiments of the invention. In general, the radiation apparatus 10 includes a structure 12 configured to support a body 14 e.g. a patient in a treatment position. The structure 12 is provided with an opening 16 to allow a portion 18 of the body 14 such as the patient's breast passing through. The radiation apparatus 10 also includes a radiation source 20 configured to be capable of generating therapeutic radiations. The radiation source 20 is movable in translational and rotational degrees of freedom. In use of the radiation apparatus 10, the radiation source 20 may deliver a therapeutic radiation toward the body portion 18. The radiation source 20 may also be configured to deliver a diagnostic radiation to the body portion 18. The radiation source 20 is capable of delivering a radiation to the body portion 18 at a wide range of positions, angles, and/or in various trajectories.

The translational and rotational motion of the radiation source 20 may be achieved by articulated arm 22, stage 24, and shoulder 26, which translate and/or rotate in multiple degrees of freedom. The articulated arm 22 and stage 24 may be secured to the floor or the inside wall of the treatment area. Articulated arms, stages, and shoulders are known to those skilled in the art. Generally, as illustrated in FIG. 1, the articulated arm may include multiple arm sections 22A, 22B, 22C that are pivotally coupled to each other by joints. Each of the arm sections 22A, 22B, 22C is pivotal about an axis, e.g., a horizontal axis, in a plane, as indicated by the arrows in FIG. 1. The articulated arm 22 may be pivotally coupled to a shoulder or shaft 26, which is coupled to the stage 24. The shoulder or shaft 26 is rotatable about an axis, e.g., a vertical axis. Depending on applications, the stage 24 may be stationary and secured to a floor or platform. Alternatively, the stage 24 may be movable in translational motions as driven by any suitable means such as motors. A pivotal mount 28 may be used to couple the radiation source 20 to the articulated arm 22. By controlling the motions of the stage 24, shoulder 26, articulated arm 22, and mount 28, the radiation source 20 may be moved in multiple degrees of translational and rotational freedom. Depending on applications, arm sections with less or more rotating or pivoting axes may be used. Sensors, encoders, cameras, and any other suitable devices may be provided to control, track, or adjust the motions of the articulated arm 22, shoulder 26 and stage 24.

For example, the radiation source 20 may be pulled closely adjacent to the body portion 18 by one or a combination of motions of the arm sections 22A-22C, shoulder 26 and stage 24. This can be advantageous in accurate delivery of a radiation dose to a target in the body portion 18. The radiation source 20 may also be positioned at a variety of angles including an angle that is substantially tangential to e.g. the chest of a patient by one or a combination of motions of the arm sections 22A-22C, shoulder 26 and stage 24. This can be advantageous in minimizing the radiation dose to the patient's heart, lung, sternum, ribs, or adjacent cartilage. The radiation source 20 may also be moved in a variety of trajectories by one or a combination of motions of the arm sections 22A-22C, shoulder 26 and stage 24, such as in linear or arc trajectories, or rotation around a vertical or horizontal axis to support a variety of treatment options. Depending on applications, a variety of positions, angles and/or motion trajectories of the radiation source 20 or any combinations are achievable for delivering a maximal radiation dose to the target tumor while minimizing dose to surrounding or adjacent healthy tissue or organs. With the present apparatus and methods, non-coplanar treatments can be advantageously performed.

Supporting Structure and Patient Orientation

In general, the structure 12 can be in any suitable form or shape to support a body 14 such as a patient in a position for radiation treatment and/or imaging. The structure 12 is provided with an opening 16 to allow a portion 18 of the body 14 such as a patient's breast passing through so that the body portion 18 is exposed to a radiation beam or at least a portion of the radiation beam. The structure 12 can be an integral part of a housing configuration in which a radiation source 20 is disposed. Alternatively, the structure 12 may be in the form of a table on which a patient 14 is supported.

The structure 12 can perform one or more of multiple functions in addition to supporting a body or patient 14. For example, the structure 12 may function to protect healthy parts of the body 14 from unnecessary irradiation. The structure 12 may also function to position and/or immobilize the body 14, or physically protect the body 14 from moving parts such as radiation source 20, and the arm etc.

The structure 12 may be constructed with any suitable materials that absorb radiation such as X-ray radiation beam. Suitable radiation absorbing materials are known in the art, which include, but are not limited to: lead, tungsten, tantalum, uranium, thorium, iridium, gold, iron, aluminum, and their alloys or mixtures or in binders that contain them including glass, plastic, and sheet rock. Near the region of the patient's breast or body portion 18, the structure 12 may be constructed with materials that have lower radiation absorption to allow penetration of the radiation to areas of interest such as the chest wall of the patient.

The opening 16 provided in the structure 12 is configured to allow a portion 18 of the body 14 passing through. For example, the opening 16 can be in circular shape to allow a patient's breast passing through. The opening 16 can also be in irregular or custom shape to allow for example, both the breast and the axillary tissue between the breast and an arm pit passing through (FIG. 2A).

Figure 2A:
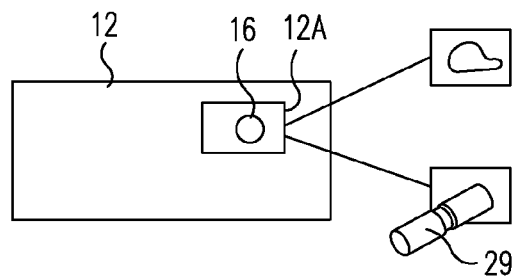
FIG. 2A illustrates a structure having a removable section in accordance with some embodiments of the invention.

In some embodiments as shown in FIG. 2A, the structure 12 may comprise a removable section 12A. The removable section 12A may be provided with an opening 16 to allow a body portion 18 passing through. The opening 16 in the removable section 12A may be customized to adapt to patients with breasts of different sizes, or adapted to different body portions such as the breast and its axillary tissue. The removable section 12A may also be used to calibrate the radiation apparatus 10. For example, a cylindrical phantom 29 may be attached to the removable section 12A and used to calibrate the isocenter, or the positions of the radiation source and/or detector.

Figure 2B:
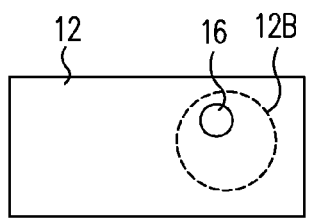
FIG. 2B illustrates a structure having a movable section in accordance with some embodiments of the invention.

In some embodiments, the structure 12 may include a movable section 12B which may e.g., rotate along the dotted line as shown in FIG. 2B. The rotatable section 12B may be provided with an opening 16 adapted to allow e.g., a breast passing through. In such embodiments, the rotatable section 12B may rotate clockwise or counterclockwise to allow e.g., the patient's left breast passing through after the right breast has been treated or irradiated.

In some embodiments, a holder (not shown) may be coupled to the structure 12 for receiving and supporting the body portion e.g., a breast. The holder may be in any suitable configuration that facilitates positioning and/or stabilizing the body portion. By way of example, the holder may be a hollow cylinder, which may include a removable end cap to allow a technician to place and position a breast in the cylinder. A gasket for sealing the breast in the holder may be provided. Vacuum means for stabilizing the breast in the holder may also be provided.

The structure 12 can be in various forms and shapes. For example, the structure 12 can be in a planar or curved shape, or formed by multiple planar or curved surfaces to form any arbitrary configurations suitable for supporting the patient in any suitable positions or orientations, such as prone, quasi prone, lying side way, standing, seating, and leaning positions. The prone and quasi-prone positions have the advantage of minimizing breast motion caused by patient's breathing and reducing unnecessary radiation exposure to healthy organs. Various means such as a breast holder may be used to stabilize the breast when the patient is in seated, standing, or leaning positions. Ultimately, the structure 12 and patient orientation may be optimized depending upon clinical issues such as treatment efficacy, side effects and patient comfort.

Figure 3A:
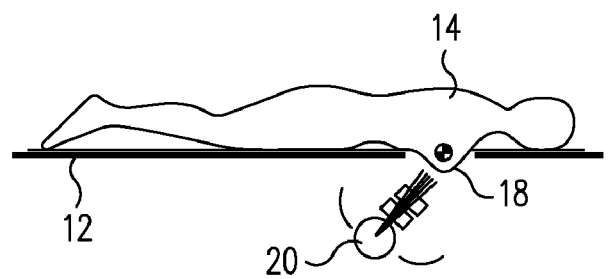
FIG. 3A is a side view illustrating a planar structure in accordance with some embodiments of the invention.
Figure 3B:
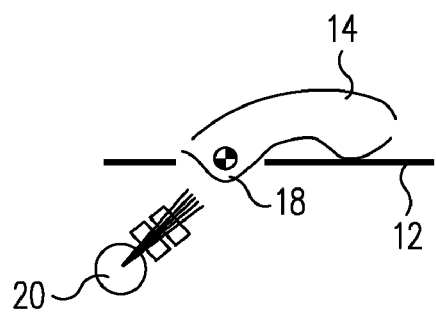
FIG. 3B is a front view illustrating a planar structure in accordance with some embodiments of the invention.
Figure 3C:
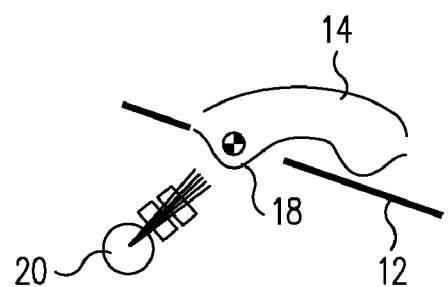
FIG. 3C is a front view illustrating an angled structure in accordance with some embodiments of the invention.

FIGS. 3A-3C illustrate some embodiments of the structure 12 which has a planar surface. The planar structure 12 may support a patient 14 in a prone or nearly prone position with a pendulous breast extending through an opening 16. A radiation source 20 is situated underneath the structure 12 and moves about the breast 18 to generate multiple treatment fields. The planar structure 12 may be on a substantially horizontal plane, as illustrated in FIGS. 3A-3B. The structure 12 may also be rolled or angled as illustrated in FIG. 3C. Angling of the structure 12 may reduce pressure on the contra-lateral breast, increase comfort to the patient, and provide better access to the treatment.

Figure 4A:
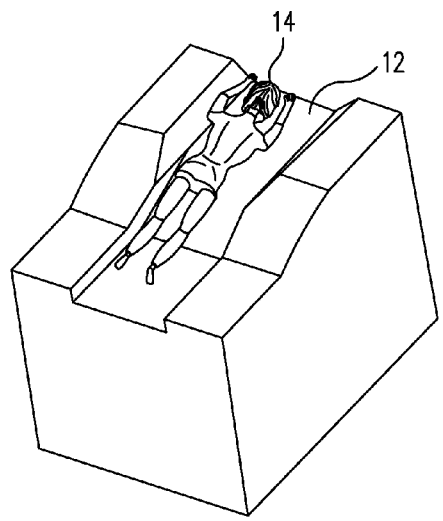
FIGS. 4A-4B illustrate a radiation apparatus including a curved structure supporting a patient in a prone or quasi-prone position in accordance with some embodiments of the invention.
Figure 4B:
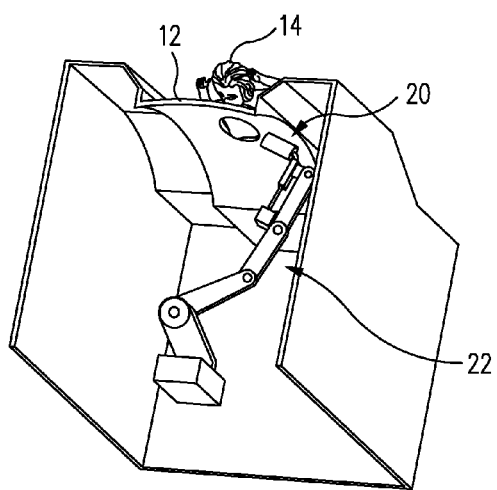

In some embodiments, the structure 12 may have a curved surface to form, e.g., a domed configuration in the cranial-caudal direction, as illustrated in FIGS. 4A-4B. A patient 14 in the cranial-caudal orientation can be positioned in a prone position with the chest being supported near the peak of the arc of the dome. This position allows more room for the patient's head and stomach, and may provide increased comfort.

Figure 5A:
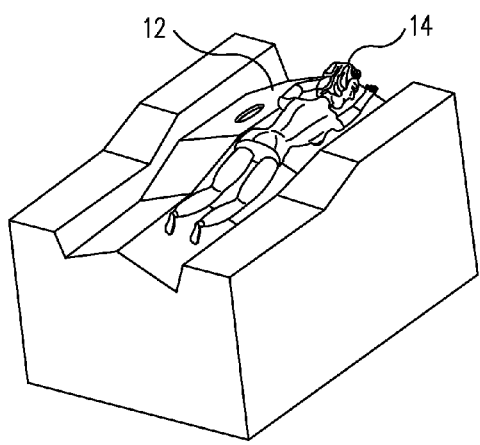
FIGS. 5A-5B illustrate a radiation apparatus including a structure formed of two angled surfaces supporting a patient in a prone or quasi-prone position in accordance with some embodiments of the invention.
Figure 5B:
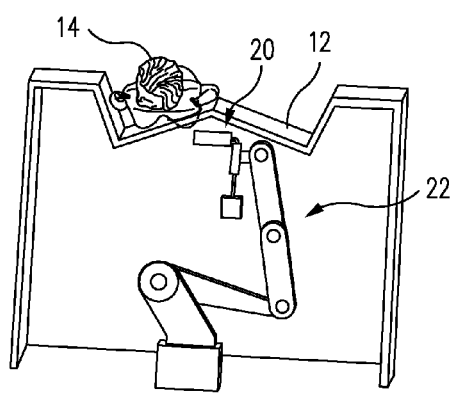

In some embodiments, the structure 12 may have two or more planar surfaces that are angled in lateral or left-right directions, as illustrated in FIGS. 5A-5B. Each of the planar surfaces may support a patient 14 in a prone or near prone position. Each of the planar surfaces may be provided with an opening for a breast extending through. With two angled surfaces each being provided with an opening, the structure 12 can accommodate patients with different breasts to be treated. For example, a patient 14 with the left breast to be treated can be supported on e.g. the first angled surface. The first angled surface reduces pressure on the right breast, and thus increase comfort to the patient. A patient 14 with the right breast to be treated can be supported on the second angled surface. The second angled surface reduces pressure on the left breast, and thus increases comfort to the patient. Each of the first and second angled surfaces may be curve- or dome-shaped, to allow more room for the head and stomach.

Figure 6A:
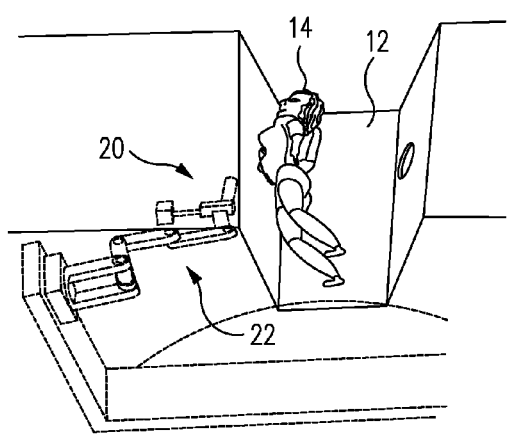
FIGS. 6A-6B illustrate a radiation apparatus including a structure supporting a patient in a lying on side position in accordance with some embodiments of the invention.
Figure 6B:
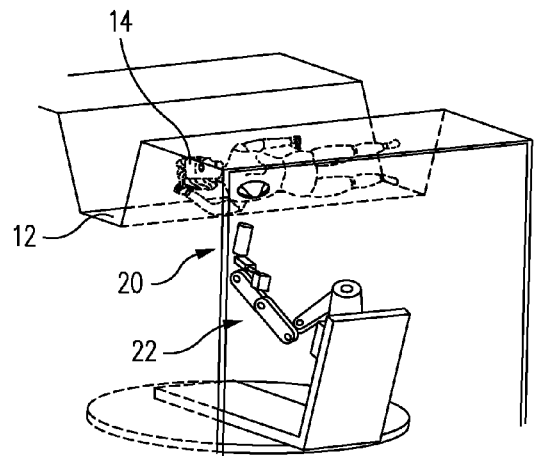

In some embodiments, the structure 12 can be configured to support a patient 14 lying on its side, as illustrated in FIGS. 6A-6B. The structure 12 may have a bottom surface and side surfaces. The side surfaces may be provided with an opening configured to allow a breast passing through when the patient 14 lies side way. The side surfaces may be angled or domed as described above to reduce pressure on the contra-lateral breast and increase comfort to the patient.

Figure 7A:
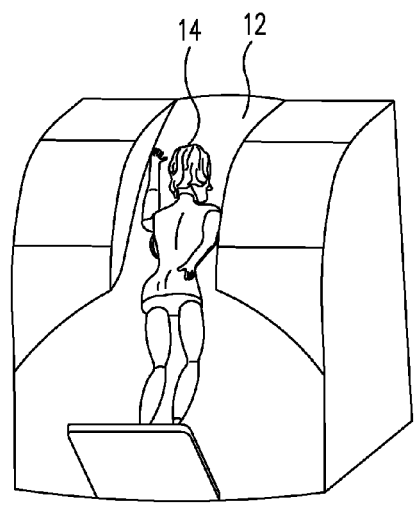
FIGS. 7A-7B illustrate a radiation apparatus including a structure supporting a patient in a leaning forward position in accordance with embodiments of the invention.
Figure 7B:
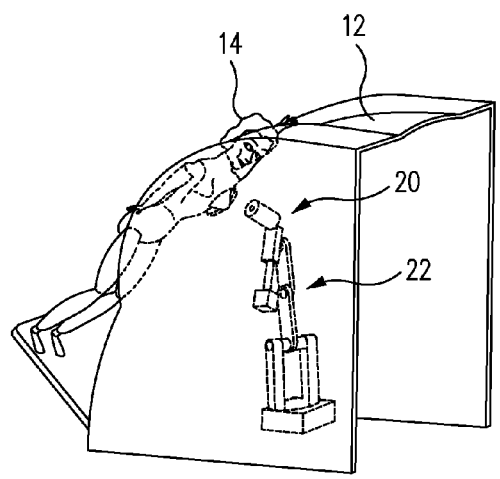
Figure 8A:
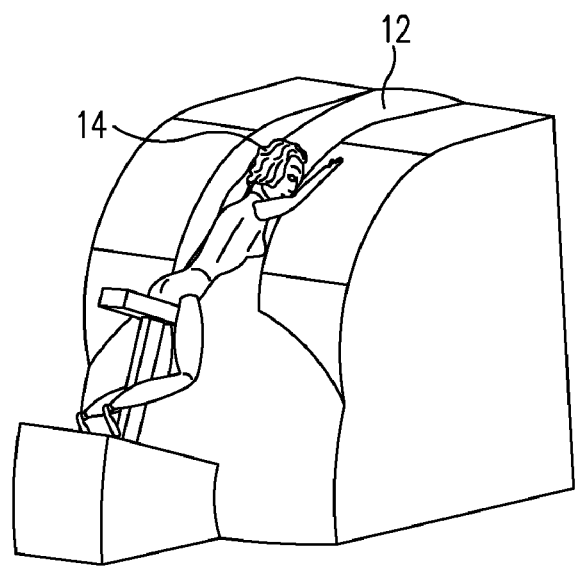
FIGS. 8A-8B illustrate a radiation apparatus including a structure supporting a patient in a leaning forward position in accordance with embodiments of the invention.
Figure 8B:
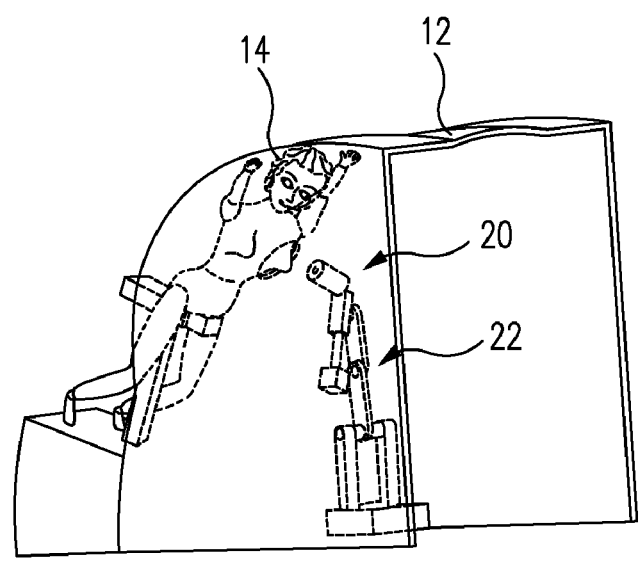

In some embodiments, the structure 12 may be configured to support a patient's torso in a leaning-forward such as substantially vertical position, as illustrated in FIGS. 7A-7B and 8A-8B. The patient 14 may be standing, as illustrated in FIGS. 7A-7B, or seated as illustrated in FIGS. 8A-8B. This configuration facilitates positioning of the breast, and improves access of the underside radiation source to the breast.

Other modifications to the structures 12 are possible and contemplated by the invention. For example, the structure 12 can be configured to support a patient's torso at any plane from horizontal to vertical, e.g., at a plane of 45 degrees with respect to a vertical axis. Alternatively, the structure 12 may be configured so that the patient 14 may be supported in one head-to-toe direction for treatment of e.g., left breast, and opposite (180 degree) head-to-toe direction for treatment of e.g., right breast.

Radiation Source

In general, the radiation source 20 and the structure 12 support a wide range of treatment options including 3-D arc therapies, intensity-modulated radiation therapy (IMRT) and 3-D conformal treatments. The radiation source 20 is movable with sufficient degrees of freedom so that a radiation beam can be delivered to a body portion 18 such as the patient's breast from a variety of positions or angles, or in various trajectories. Preferably, the radiation source 20 is movable in both translational and rotational degrees of freedom.

Figure 9:
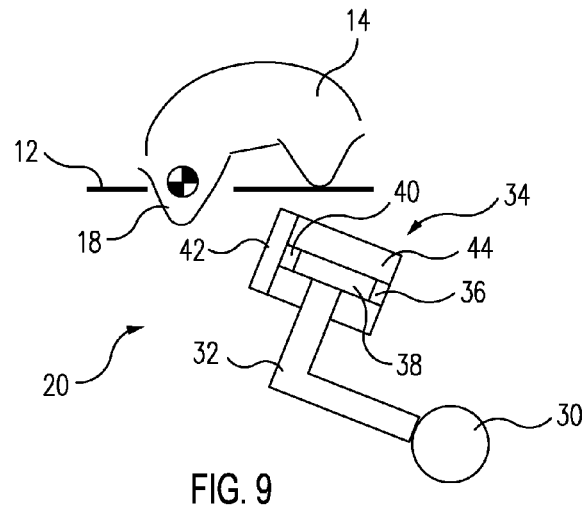
FIG. 9 illustrates a radiation apparatus including an X-ray source and a structure supporting a patient in a prone position in accordance with some embodiments of the invention.

FIG. 9 illustrates a radiation source 20 that can be used in the radiation apparatus 10 of the invention. For purposes of illustration, the radiation source 20 in FIG. 9 is shown in conjunction with a planar structure 12 that supports a patient 14 in a prone position. It will be appreciated that the radiation source 20 can be configured in conjunction with a structure 12 in other suitable forms or shapes to support a patient in a variety of orientations or positions as described above.

The radiation source 20 can be any source that generates radiation beam suitable for radiation treatment. For example, the radiation source 20 may be a source that generates X-ray beams, proton beams, carbon ion beams, electron ray beams, positron beams, antiproton beams, neutron beams, alpha ray beams, muons and pions etc. By way of example, the radiation source 20 may be an X-ray source configured to generate X-ray beams suitable for therapeutic treatment, or suitable for diagnostic imaging. Alternatively, the radiation source 20 can be configured to be capable of generating both radiation beams for imaging and radiation beams for treatment. In general, the X-ray source 20 may be configured to generate radiation beams with energy levels ranging from 30 KV to 6 MV or higher. As used herein, energy levels are expressed in terms of electric potential used by an accelerator or X-ray tube to produce photon beam. For example, in some embodiments, it would be desirable to employ X-ray tubes as radiation source 20 to generate beams with energy levels ranging from about 120 KV to about 1 MV, or preferably from about 200 KV-300 KV for therapeutic treatment. This would provide a good combination of low skin dose with moderate X-ray shielding requirements. In some embodiments, it would be desirable to employ accelerators as radiation source 20 to generate beams with energy levels ranging from about 900 KV to about 6 MV or higher for therapeutic treatment. For diagnostic imaging of soft tissue such as breasts, in some embodiments it would be desirable to use radiations generated by X-ray tubes operating at from about 30 KV to 1 MV or higher, or preferably from about 50 KV to about 80 KV. Radiations generated by accelerators operating at as high as 1 MV or higher may also be used to obtain relatively lower contrast images sufficient for positioning. In some embodiments where metal surgical clips or implanted gold seeds etc. are used as fiducial markers for e.g. breast positioning, radiation beams with energy levels ranging from about 30 KV to multi-MV may be used. U.S. Pat. No. 6,888,919 describes an X-ray radiation source that is capable of generating X-rays at different energy levels, the disclosure of which is incorporated herein by reference in its entirety.

The X-ray source 20 may comprise a linear accelerator (LINAC) as shown in FIG. 9. The linear accelerator may include a microwave source 30 such as magnetron, a waveguide 32, and a head unit 34. The head unit 34 holds an X-ray generator 36 such as an electron gun, an accelerator 38, and a target 40. The head unit 34 may further include a beam adjuster 42 placed at a front end of the head unit 34 and shielding 44 as needed. In operation, the electron gun 36 is activated to emit electrons. The electrons are accelerated by the accelerator 38 which is arranged between the electron gun 36 and the target 40. The acceleration of electrons is controlled by microwaves which are generated by the microwave source 30 and supplied via the waveguide 32. The accelerated electrons strike the target 40, and X-rays are generated. The generated X-rays may be collimated by the beam adjustor 42, which will be described in more detail below. The accelerator may be configured to generate beams for therapeutic treatment, or for both therapeutic treatment and diagnostic imaging. For instance, the accelerator may be operated at beam energies ranging from about 900 KV to about 6 MV or higher to generate beams suitable for therapeutic treatment. The accelerator may also be operated at beam energies up to 1 MV or higher to generate beams for obtaining lower contrast images suitable for positioning.

The radiation source 20 is capable of delivering a radiation beam to the body portion or breast 18 from a small tangential angle (shallow angle with respect to the chest wall), e.g., 0-20 degrees. To achieve the small tangential angle, in some embodiments, the head unit 34 is designed to be narrow and short. In some embodiments, the microwave source 30, the waveguide 32, and head unit 34, may be in certain configuration such as L- or T-shape to help achieve small tangential angle views and maximize clearance to the structure 12. In some embodiments, the amount of radiation shielding 44 surrounding the accelerator 38 and the beam adjustor 40 can be minimized. In some embodiments, the output of the radiation source 20 can be selected so that smaller x-band accelerator may be used. For instance, the output of the source 20 can be in the range of 1-5 Gy/min at 1-4 MV at an about 100 cm distance or less from the focal spot. In some embodiments, smaller microwave source 30 such as magnetron is used to drive the accelerator 38 to reduce the size or cost of the X-ray source 20. In some embodiments, a bent RF waveguide 32 is used to form certain configurations. Various combinations of designs may be used to achieve small tangential angle view.

Figure 10:
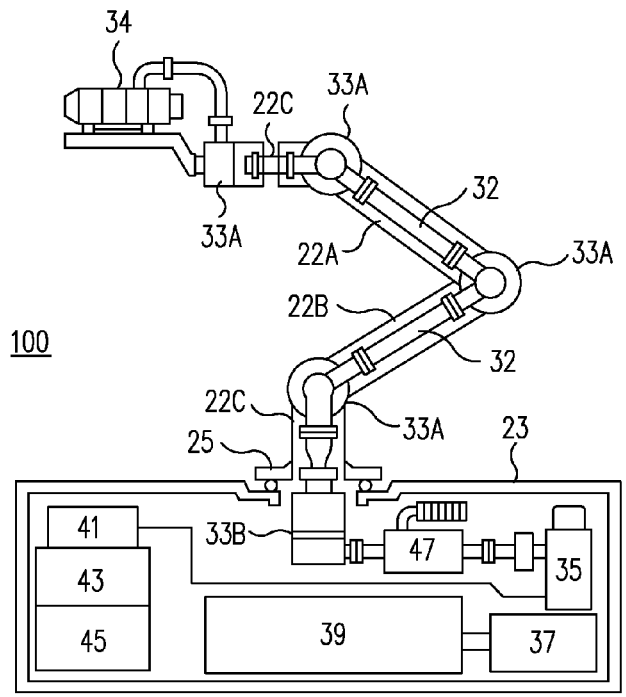
FIG. 10 is a schematic illustrating a radiation apparatus in accordance with some embodiments.

FIG. 10 illustrates a radiation apparatus 100 where one or more rotary waveguide joints 33A, 33B are used. The use of rotary waveguide joints allows the waveguide 32 to extend its length down the articulated arm 22 while still permitting the arm 22 to articulate freely. This enables the accelerator head unit 34 to be mounted proximate to the very end of the articulated arm 22, and allows the microwave source such as a klystron and other heavy RF components to be mounted relatively remotely from the head unit 34 such as in the arm base 23, or distributed along the sections of the arm 22.

As illustrated in FIG. 10, the microwave source components may include a klystron 35, pulse transformer 37, pulse forming network ("PFN") 39, RF driver 41, solenoid supply 43, ARM servo motor drives 45, and circulator 47. Klystron 35 is a high voltage device. A klystron would be desirable to drive higher power accelerators that can deliver the required radiation dose to the patient in a short period of time. The klystron 35 is enclosed in a magnetic solenoid to focus the electron beam. The solenoid is heavy, considerably heavier than the weight of the klystron itself. The klystron 35 is coupled to and typically mounted vertically above the pulse transformer 37, which is enclosed within a tank of transformer oil. The pulse transformer 37 is a heavy component and typically weighs many hundreds of pounds. The circulator 47 acts a kind of one-way valve for microwave energy to protect the klystron 35 by diverting and absorbing any microwave energy that is reflected back from the accelerator 34. The circulator 47 may also be disposed on the arm 22 if there is insufficient room for it in the base 23.

One or more U-type rotary waveguide joints 33A may be coupled to an arm joint or elbow, which couples pivotal arm sections such as 22A and 22B. As arm sections 22A and/or 22B move or rotate around a pivotal axis, the waveguide joints 33A also move or rotate. This causes the waveguide 32 to articulate with the robotic arm 22 without changing the overall length of the waveguide 32, hence avoiding phase shift in the radio frequency entering the accelerator 34. The rotary U-joints 33A may be disposed across over from one side to the other of the arm 22 at each arm pivot point. Alternatively, the U-joints 33A and the waveguide run 32 may be mounted on one side of the arm 22, as shown in FIG. 10, so long as the rotation axis of each waveguide joint is aligned on the axis of the adjacent arm pivot. An L-type rotary waveguide 33B may be used to couple the circulator 47 in the turntable 25 in the base 23. At the front end of the articulated arm 22 a wrist shaft 22C may be coupled to adjacent U-joints 33A through the hollow center bores in the joints. This allows the accelerator head unit 34 to be rotated about the end axis of the arm 22 to provide an additional degree of freedom of movement.

Figure 11A:
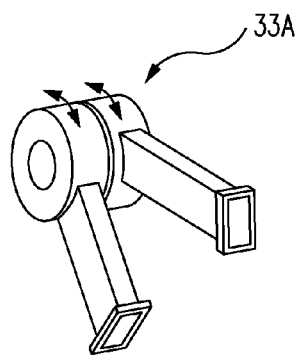
FIGS. 11A-11C are schematics illustrating some embodiments of rotary waveguide joints.
Figure 11B:
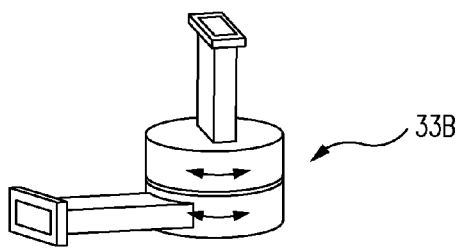
Figure 11C:
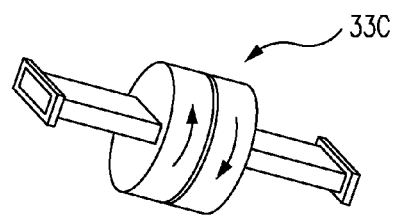

The use of rotary waveguide joints 33A, 33B may advantageously position the heavy microwave source components in the arm base 23. As a result, the load on the front end of the arm 22 would be much lower. The reduced weight and bulk at the end of the arm 22 would in turn permit the accelerator head unit 34 to be positioned at the preferred angles and locations close to the patient. FIGS. 11A, 11B, and 11C show exemplary U-type 33A, L-type 33B, and wrist type 33C rotary waveguide joints respectively.

In some embodiments, the radiation source 20 may include an X-ray tube configured to generate therapeutic radiation. The X-ray tube may be mounted proximate to the end of the articulated arm 22 and moved by the arm as described above. The X-ray tube may be custom-designed such that the tube may be brought very close to e.g., the patient's torso, and as such, the X-ray photon beam emerges from the tube closely adjacent to or tangential to the chest wall. This would be desirable to deliver treatment plans that minimize the dose to the intercostal cartilage, heart, lung etc. One of the advantages of using an X-ray tube as a radiation source is that the thickness of shielding needed is much less than is necessary for a linear accelerator. The use of an X-ray tube may also reduce the weight and cost the treatment machine and desirably, make access to the patient easier and enable more optimal treatment beam angle. The X-ray tube can also serve as the X-ray source for imaging by operating it at reduced voltages such as from 30 KV upwards, or preferably from about 50 KV to about 80 KV. U.S. patent application Ser. No. 11/944,188 filed Nov. 21, 2007 entitled "X-ray Tube Having a Focal Spot Proximate the Tube End" discloses an X-ray tube that can be used with the radiation apparatus of this invention. The X-ray tube reduces the spacing between the focal spot of an anode and an adjacent end wall of the evacuated enclosure in which the anode is disposed. This positions the tube relatively closer to e.g. the chest wall of a patient during a radiation procedure. U.S. patent application Ser. No. 11/944,188 is incorporated herein by reference in its entirety. The X-ray tube may be operated at high voltages to generate X-ray beams suitable for treatment, such as with energy levels from about 120 KV to about 1 MV, or preferably from about 200 KV to about 300 KV, which provides a good combination of low skin dose with moderate X-ray shielding requirements. A liquid-metal cooling system may be used to efficiently transfer heat from the target to the cooled endplate of the tube. By this or other cooling means the tube can operate continuously at a high average beam power with plenty of safety margin, and deliver the required radiation dose for a breast treatment fraction in e.g. approximately five minutes.

The beam adjuster 42 may be a four-blade (or jaw) collimator each of the blade is independently controlled. The beam adjustor 42 may also be a multi-leaf collimator. Multi-leaf collimators are known to those skilled in the art. In general, a multi-leaf collimator includes a plurality of pairs of opposing veins or leaves made of materials that effectively block the radiation generated by the radiation source. Each pair of the leaves is controllably movable relative to each other. By driving each leaf into different positions, various sizes and shapes of the radiation beam can be formed and the intensity of the radiation beam can be modulated.

The number of leaves in a multi-leave collimator can have a wide range. Generally, a multi-leave collimator having a large number of narrow leaves has a higher resolution than a multi-leave collimator having a small number of thick leaves. A high resolution is generally beneficial in shaping the radiation beam precisely to the shape of the tumor and modulating the radiation intensity precisely.

The leaves may be flat, curved, or any suitable shape, and in any suitable configuration. For example, in some embodiments, the leaves move horizontally (parallel to the structure plane supporting the patient) and not vertically so to reduce the chances of interference between the beam adjustor and the structure.

In some embodiments, the beam adjuster 42 may include two or more multiple leaf collimators, with one collimator superimposed over another collimator. The multiple leaves in one collimator are at an angle, e.g., 45 or 90 degrees with respect to the multiple leaves in another collimator. Such an arrangement of two or more multi-leave collimators superimposed over each other allows shaping of the radiation beam in more diverse shapes. It should be noted that other beam adjuster such as interchangeable fixed shaped nozzles may be used for e.g. proton radiation sources.

The design, configuration of the radiation source 20 and support structure 12, in combination with the articulated arm 22, shoulder 26, and stage 24 provide a broad range of motion of the radiation source 20 and enable various treatment plans. In a simple configuration, the radiation source 20 may rotate around a vertical axis, e.g., a breast nipple axis when the patient is in prone position, to deliver a half-cone radiation beam to the breast. In a more complicated configuration, the radiation source 20 may rotate around the nipple axis and the source 20 and/or supporting structure 12 may move translationally in the x, y, and z directions to adjust the distance from the radiation source 20 to the breast 18. In a still more complicated configuration, the position of the radiation source 20 may be adjustable in six degrees of freedom to allow the source 20 to point at any part of the breast 18 from any angle around the breast with any desired source-to-breast distance ($\gamma$).

Figure 12A:
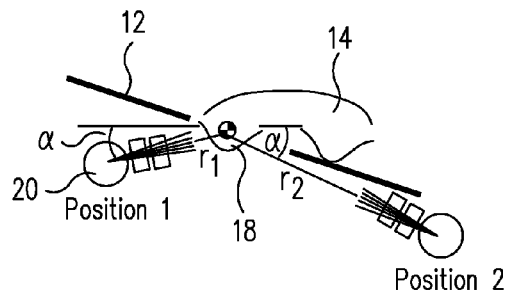
FIGS. 12A-12C illustrate a radiation apparatus including a radiation source movable at various distances and angles with respect to the patient's breast in accordance with some embodiments of the invention.
Figure 12B:
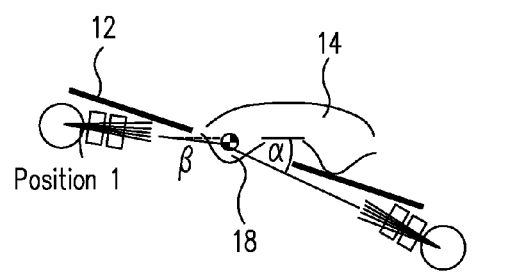
Figure 12C:
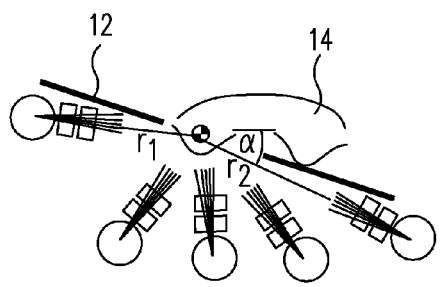

FIGS. 12A-12C illustrate some exemplary configurations of the radiation source 20 and the structure 12 on which a body 14 is supported. In the embodiments shown in FIGS. 12A-12C, the structure 12 is angled with respect to a horizontal plane to provide more comfort to the patient 14. To achieve a tangential view of a target in the breast 18, the angles of the radiation source 20 with respect to the horizontal plane, or the source-to-breast distances ($\gamma$) may be adjusted. For example, to achieve a given tangential angle ($\alpha$) view, the radiation source 20 may be pulled away from the breast as the radiation source 20 moves from position 1 to position 2 (FIG. 12A). Likewise, by moving the radiation source 20, different tangential angle views can be achieved at a given source-breast distance. For example, as shown in FIG. 12B, a smaller tangential angle ($\beta$) view can be achieved when the radiation source 20 is in position 1 as compared to position 2 ($\alpha$). The translational and rotational degrees of freedom allow the source 20 to deliver radiation beams from a wide range of positions to achieve a broad range of tangential angle views, as illustrated in FIG. 12C.

Imaging (Detector-Source) Configuration

The radiation apparatus 10 may include real time X-ray projection and tomographic imaging capability (computed tomography or CT and tomosynthesis) to improve targeting accuracy and allow for treatment planning. Imaging may occur with or without implanted fiducial markers. The imaging source may be the same as the treatment source or may be a separate source that would preferentially operate at lower energies than the treatment beam e.g., at 50-130 keV energy level. An amorphous silicon based flat panel detector may be used as the image detector. Discrete crystalline or polycrystalline detectors may also be used. For computed tomography, both the source and detector may move around an isocentric point conforming to a $3^{rd}$ generation CT geometry, or the detector(s) may be stationary to conform to a $4^{th}$ generation geometry. The radiation system may include linear or circular tomosynthesis capabilities.

Figure 13:
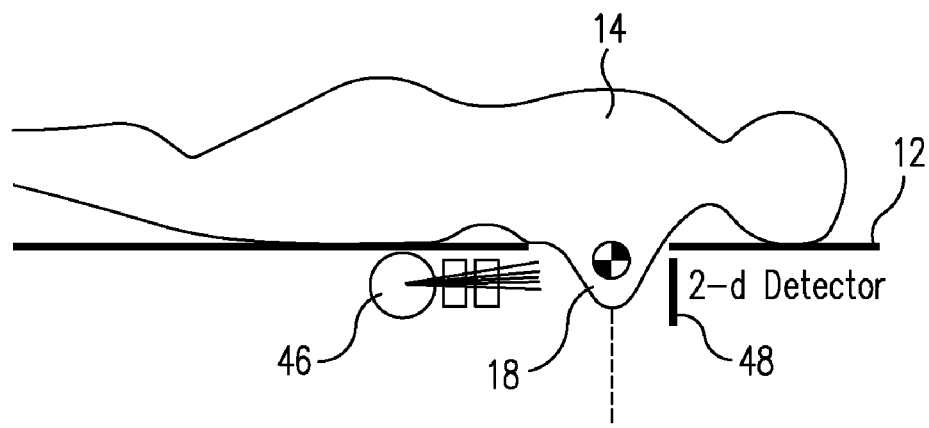
FIG. 13 illustrates a radiation apparatus including an imaging source and an image detector in accordance with one embodiment of the invention.

FIG. 13 illustrates an embodiment in which an imaging source 46 and a detector 48 are disposed on a same side of the structure 12, e.g., underneath the structure 12. The detector 48 can be a planar (2-d) detector and positioned opposite to the source 46. In some embodiments, the source 46 and detector 48 rotate around the nipple axis allowing for cone-beam CT acquisition and reconstruction of HU values for treatment planning. Partial rotations (<180 degree+fan) can be used for tomosynthesis. Alternative tomosynthesis geometries include lateral motion where the detector 48 is translated in one direction and source 46 is translated in the opposite direction. A $4^{th}$ generation cone-beam geometry is supported by using fixed stationary detectors situated on an outer arc.

In some embodiments, an independent robotic arm may be used to control the source 46. For example, the imaging source 46 and detector 48 may move in translational and/or rotational degrees of freedom in a more complicated trajectory, e.g., not-coplanar. This trajectory may better enable imaging of the patient's lymph nodes and chest wall.

Figure 14:
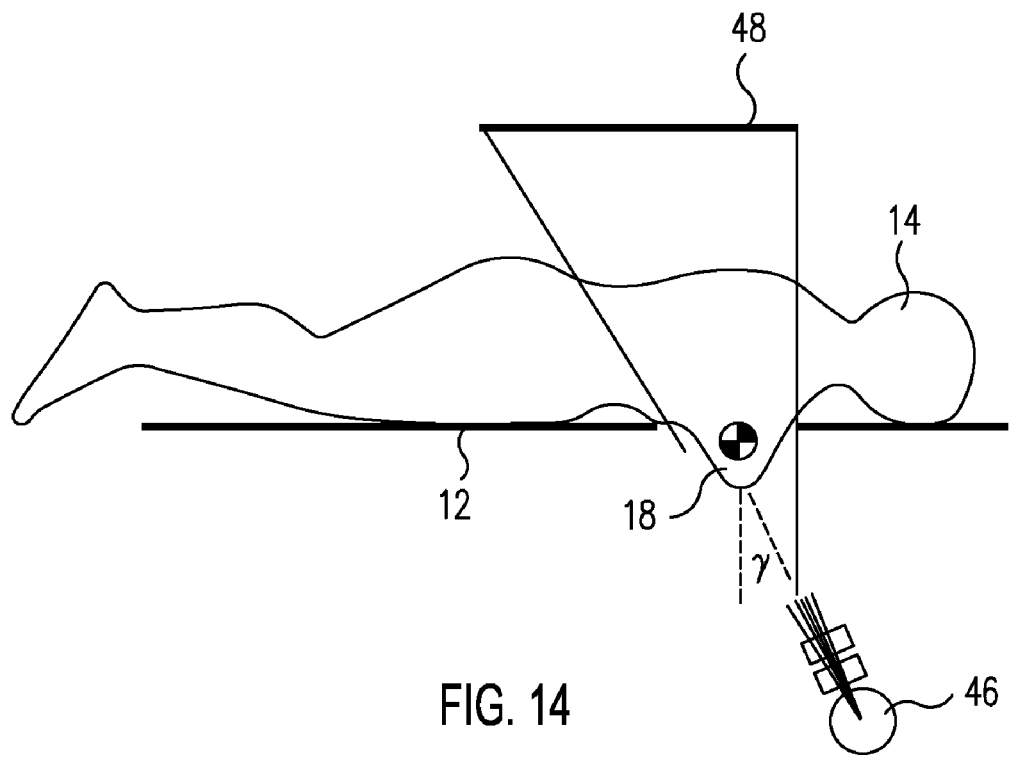
FIG. 14 illustrates a radiation apparatus including an imaging source and an image detector in accordance with another embodiment of the invention.

FIG. 14 illustrates an embodiment in which the imaging source 46 and the detector 48 are disposed on the different sides of the structure 12. For example, in a geometry where a patient is supported on the structure 12 in a prone position, the imaging source 46 may be disposed under the structure 12 and the detector 48 is over the structure 12. A 2-D planar detector 48 may be located behind or posterior to the patient 14. Anterior/posterior (A/P) projection images through the breast and chest may be obtained. The detector 48 and source 46 may also rotate together, for example, around the nipple axis to achieve circular tomosynthesis acquisitions and reconstruction capabilities. The tomosynthesis geometry may be linear or arc. Spatial resolution in the patient's A/P direction depends on the tomosynthesis angle (γ) shown in FIG. 14. In comparison with the geometry where the source and the detector are underneath the structure, this geometry has the benefit of permitting for visualization of the chest wall. In some embodiments, the angle (γ) may be made to be sufficiently large, e.g., 20-60 degrees so that sufficiently good reconstructions may be obtained to enable treatment planning and/or more accurate targeting. In some embodiments, the planar detector 48 is sufficiently large, e.g., equal or more than 20 cm so that rotation of the detector 48 along with the source 46 is not required. In some embodiments, two or more detectors may be disposed above the structure 12. One of the advantages of using two or more detectors is that the detectors can be disposed at fixed positions with respect to the radiation source 46, and are not required to be movable with the radiation source 46, although they can be movable in alternative embodiments.

Tomographic reconstructions of acquired images are known and they are not described herein in order to simply the description of the invention. Various processing techniques may be used including filtered backprojection, backprojection and filtering, or iterative methods including ART, EM, MAP etc.

Treatment Options

The radiation system of the invention supports multiple different treatment options, including intensity-modulated radiation therapy (IMRT), arc therapy, and 3-D arc therapy. The imaging capabilities such as tomosynthesis and CBCT described above allow for accurate 3-D localization of e.g. the breast and chest wall. This information can be used to adjust the position of the patient, the supporting structure, and the radiation source to properly target the treatment.

In intensity-modulated radiation therapy, a multi-leaf collimator may be used as a beam adjustor. The radiation dose can be designed to conform to the size, shape, and location of the cancer by modulating or controlling the intensity of the radiation beam with the multi-leaf collimator. Treatment can be planned by using computed tomography (CT) or cone beam CT (CBCT) images in conjunction with computerized dose calculations to determine the dose intensity pattern that best conforms to the cancer size and shape. The radiation source may rotate about an axis such as the nipple axis. The distance between the radiation source and the breast, and angle of the radiation source with respect to the breast may be adjusted using an articulated arm and stage.

Arc therapy is a form of intensity-modulated radiation therapy. The radiation source moves in an arc geometry to deliver therapeutic radiation from a variety of angles. A multi-leaf collimator may be used to modulate the intensity as the radiation source is on and moving around the target. For example, in operation, the radiation source may rotate about an axis such as the nipple axis. The distance between the radiation source and the breast may be adjusted using an articulated arm and stage.

In a 3-D arc therapy, a simple collimator consisting of 4 independent blades may be used as a beam adjustor. In operation, the motion of the radiation source and/or supporting structure may be driven by a robotic arm. The distance between the radiation source and the breast, and angle of the radiation source with respect to the breast may be adjusted using an articulated arm.

From the foregoing it will be appreciated that, although specific embodiments of the invention have been described herein for purposes of illustration, various modifications may be made without deviating from the spirit and scope of the invention. For instance, the structure may be in the form of a table which may be moved by a robot arm in translational and rotational degrees of freedom. All the modifications are contemplated by the invention.

What is claimed is:

1. A radiation apparatus, comprising:
 a radiation source; and
 a structure providing a housing that encloses at least a portion of the radiation source therein, a portion of the structure being adapted to support a body and provided with an opening to allow a portion of the body passing through into the housing to be exposed to at least a portion of a radiation generated by the radiation source while in use;
 wherein said radiation source is adapted to be movable in three translational and three rotational degrees of freedom.

2. The apparatus of claim 1 wherein the radiation source comprises a radiation source configured to generate therapeutic radiation.

3. The apparatus of claim 2 wherein the radiation source comprises an X-ray source configured to generate X-ray beams with energy at megavoltage levels.

4. The apparatus of claim 1 wherein the radiation source is configured to be capable of generating therapeutic radiation and diagnostic radiation.

5. The apparatus of claim 1 wherein the radiation source comprises an X-ray tube configured to generate X-ray beams with energy from about 30 KV to about 6 MV.

6. The apparatus of claim 1 wherein the radiation source is a linear accelerator comprising a radiation generator, a microwave source, and a waveguide, said waveguide being movable relative to the radiation generator and/or microwave source.

7. The apparatus of claim 1 wherein the portion of the structure is adapted to support a patient and provided with an opening adapted to allow a breast of the patient passing through.

8. The apparatus of claim 1 wherein the portion of the structure is adapted to support a patient and provided with an opening adapted to allow a breast and tissue between the breast and an arm pit passing through.

9. The apparatus of claim 1 wherein the portion of the structure is adapted to support a patient in a prone position.

10. The apparatus of claim 1 wherein the portion of the structure is adapted to support a patient lying on its side.

11. The apparatus of claim 1 wherein the portion of the structure is adapted to support a patient in a forward-leaning position.

12. The apparatus of claim 1 wherein the portion of the structure is adapted to support a patient's torso in a substantially upright position.

13. The apparatus of claim 1 wherein the portion of the structure is adapted to support a patient in a prone position and the radiation source is rotatable about a horizontal axis in about 180 degrees.

14. The apparatus of claim 1 wherein the portion of the structure is adapted to support a patient's torso in a substantially upright position, and the radiation source is rotatable about a vertical axis in about 180 degrees.

15. The apparatus of claim 1 wherein the portion of the structure is adapted to support a patient in a substantially prone position and disposed to form a non-zero angle with respect to a horizontal plane.

16. The apparatus of claim 1 wherein the portion of the structure comprises two surfaces each being provided with an opening adapted to allow a patient's breast passing through, said two surfaces are angled, each being adapted to support a patient in a substantially prone position.

17. The apparatus of claim 1 which is adapted for intensity-modulated radiation therapy.

18. The apparatus of claim 1 which is adapted for arc therapy.

19. A radiation apparatus, comprising:
a radiation source; and
a structure providing a housing that encloses at least a portion of the radiation source therein, a portion of the structure being adapted to support a body and provided with an opening to allow a portion of the body passing through into the housing to be exposed to at least a portion of a radiation generated by the radiation source while in use;
wherein said radiation source is adapted to be movable at least in a translational direction; and
further comprising a second radiation source adapted to generate a radiation for imaging the body portion and an image detector disposed operatively opposite to the second radiation source.

20. The apparatus of claim 19 wherein the second radiation source and the image detector are operatively disposed on a same side of the portion of the structure.

21. The apparatus of claim 19 wherein the second radiation source and the image detector are operatively disposed on opposite sides of the portion of the structure.

22. A radiation apparatus, comprising:
a radiation source; and
a structure providing a housing that encloses at least a portion of the radiation source therein, a portion of the structure being adapted to support a body and provided with an opening to allow a portion of the body passing through into the housing to be exposed to at least a portion of a radiation generated by the radiation source while in use;
wherein said radiation source is adapted to be movable at least in a translational direction; and
wherein the portion of the structure has a curved-surface forming a dome configuration, and said opening is provided near the peak of the dome.

23. An apparatus for radiation treatment of breast cancer, comprising
a structure providing a housing, a portion of the structure being adapted to support a patient in a position and provided with an opening to allow a breast of the patient passing through into the housing; and
a radiation source configured to generate a therapeutic radiation to the breast, wherein at least a portion of said radiation source is enclosed inside the housing and movable in translational and rotational degrees of freedom, thereby being capable of delivering at least a portion of the therapeutic radiation to at least a portion of the breast at an adjustable distance between the radiation source and the breast, from an adjustable angle to the breast, and/or in an adjustable trajectory.

24. The apparatus of claim 23 wherein the radiation source is an X-ray source capable of generating X-ray beams with energy at megavoltage levels.

25. The apparatus of claim 23 wherein the radiation source is movable in three translational and three rotational degrees of freedom.

26. The apparatus of claim 23 further comprising a second radiation source configured to generate a diagnostic radiation, and an image detector disposed operatively opposite to the second radiation source.

27. The apparatus of claim 26 wherein the second radiation source and the image detector are disposed operatively on a same side of the portion of the structure.

28. The apparatus of claim 26 wherein the second radiation source and the image detector are disposed operatively on opposite sides of the portion of the structure.

29. The apparatus of claim 23 wherein the radiation source is configured to be capable of generating a diagnostic radiation.

30. The apparatus of claim 23 wherein the portion of the structure is adapted to support the patient in a prone position.

31. The apparatus of claim 23 wherein the portion of the structure is adapted to support the patient in a forward-leaning position.

32. The apparatus of claim 23 wherein the portion of the structure is adapted to support the patient's torso in a substantially upright position.

33. The apparatus of claim 23 wherein the portion of the structure is adapted to support a patient in a prone position and disposed to have a non-zero angle with respect to a horizontal plane.

34. The apparatus of claim 23 wherein the portion of the structure has a curved-surface forming a dome configuration, and said opening is provided near the peak of the dorm.

35. The apparatus of claim 23 wherein the radiation source comprises an X-ray tube configured to generate X-ray beams with energy from 200 to 800 KV.

36. The apparatus of claim 23 wherein the radiation source is a linear accelerator comprising a radiation generator, a microwave source, and a waveguide, said waveguide being movable relative to the radiation generator and/or microwave source.

37. A radiation method, comprising the steps of:
providing a radiation apparatus including a radiation source and a structure providing a housing that encloses at least a portion of the radiation source therein, a portion of the structure being configured to support a body and provided with an opening allowing a portion of the body to pass through into the housing, and the radiation source being movable in three translational and three rotational degrees of freedom;
positioning a body on the portion of the structure allowing a portion of the body passing through into the housing; and
delivering a radiation to the portion of the body using the radiation source.

38. The method of claim 37 wherein the step of delivering the radiation comprises modulating the intensity of the radiation.

39. The method of claim 37 wherein the step of delivering the radiation comprises delivering the radiation in an arc geometry.

40. The method of claim 37 wherein the step of delivering comprises delivering a radiation for therapeutic treatment of cancer.

41. The method of claim 40 wherein the radiation has energy at megavoltage levels.

42. The method of claim 40 further comprising the step of delivering a radiation for imaging the body portion, and acquiring a data set using the imaging radiation.

43. The method of claim 42 wherein the step of delivering the imaging radiation comprises delivering in a linear geometry.

44. The method of claim 42 wherein the step of delivering the imaging radiation comprises delivering in an arc geometry.

45. A radiation apparatus, comprising:
a radiation source capable of generating a radiation for therapeutic treatment; and
a structure providing a housing that encloses at least a portion of the radiation source therein, a portion of the structure being adapted to support a body and provided with an opening to allow a portion of the body passing through into the housing to be exposed to at least a portion of the radiation while in use;
wherein said radiation source is adapted to be rotatable about a substantially vertical axis; and
wherein the radiation source is adapted to be movable in three translational and three rotational degrees of freedom.

46. A radiation apparatus, comprising:
a radiation source capable of generating a radiation for therapeutic treatment; and
a structure providing a housing that encloses at least a portion of the radiation source therein, a portion of the structure being adapted to support a body and provided with an opening to allow a portion of the body passing through into the housing to be exposed to at least a portion of the radiation while in use;
wherein said radiation source is adapted to be rotatable about a substantially vertical axis; and
wherein the portion of the structure is adapted to support a patient in a substantially prone position to allow a breast of the patient passing through the opening into the housing, and the radiation source is further adapted to be rotatable about a substantially horizontal axis in about 180 degrees.

* * * * *